United States Patent [19]

Nyeki et al.

[11] Patent Number: 5,273,960
[45] Date of Patent: Dec. 28, 1993

[54] HIGH PURITY CRYSTALLINE PEPTIDES ARGLYSASP AND ARGLYSASPVAL AND A PROCESS FOR THEIR PREPARATION

[75] Inventors: Olga Nyeki; Istvan Schon, both of Budapest, Hungary; Laszlo Denes, Ramat-Gan, Israel; György Hajos, Budapest, Hungary; Laszlo Szporny, Budapest, Hungary; Geza Ivanyi, Taksony, Hungary; Tamas Überhardt, Budapest, Hungary; Lajos Kovacs, Budapest, Hungary; Imre Peter, Budapest, Hungary; Maria Gazdag, Budapest, Hungary; Zsuzsanna Muck, Budapest, Hungary; Iidiko Überhardt, Budapest, Hungary; Gizella Lorant, Monor, Hungary

[73] Assignee: Richter Gedeon Vegyeszeti Gyar Rt., Budapest, Hungary

[21] Appl. No.: 748,943

[22] Filed: Aug. 23, 1991

[30] Foreign Application Priority Data

Aug. 23, 1990 [HU] Hungary ................................. 5284

[51] Int. Cl.$^5$ ........................ C07K 5/00; C07K 5/08; C07K 5/10
[52] U.S. Cl. .................................. 514/018; 530/331; 530/330
[58] Field of Search .................. 530/331, 330; 514/18

[56] References Cited

U.S. PATENT DOCUMENTS 4,428,938  1/1984  Kisfaludy et al. ................. 424/177

Primary Examiner—Lester L. Lee
Assistant Examiner—Carol A. Salata
Attorney, Agent, or Firm—Herbert Dubno; Jonathan Myers

[57] ABSTRACT

The present invention relates to a process for the preparation of high purity crystalline peptides Arg Lys Asp hydrate acetate and Arg Lys Asp Val from crude, amorphous peptides Arg Lys Asp and Arg Lys Asp Val hydrate acetate.

The process is characterized in that
  the crude, amorphous peptide Arg Lys Asp or Arg Lys Asp Val is let stand at room temperature in 5 to 20 unit volume of ethanol containing 0.5 to 4.0% by volume of acetic acid and 5 to 25% by volume of water, wherein the volume unit is calculated for the mass unit of the material and mass unit relates to volume unit as g relates to ml,
  then the crystallized peptide is separated from the crystalline suspension, preferably after cooling.

11 Claims, No Drawings

HIGH PURITY CRYSTALLINE PEPTIDES ARGLYSASP AND ARGLYSASPVAL AND A PROCESS FOR THEIR PREPARATION

FIELD OF THE INVENTION

The invention relates to crystalline peptides Arg Lys and Arg Lys Asp Val of high purity, to pharmaceutical compositions containing them and to a process for the preparation of these peptides and compositions.

BACKGROUND OF THE INVENTION

The Hungarian patent specification No. 185,263 discloses the peptides Arg Lys Asp and Arg Lys Asp Val and their action influencing the immune system. Several publications describe their wide-range in vitro and in vivo immunological and immunopharmacological effects: see e.g. Hoope Seyler's Z. Physiol. Chem., 364, 933. (1983); J. Immunopharmacol., 7, 67 (1985); Int. J. Immunopharmacol., 8, 167 (1986); Immunpharmacol. Immunotoxicol., 9, 1 (1987).

With the knowledge of the advantageous biological results detailed toxicological and clinical examination of these two peptides has been commenced. For the preparation of a clinically usable drug the synthesis of the peptides has to be carried out on industrial scale of the magnitude of several kilogramms so that high purity products be prepared which correspond to the strict stipulations determined for pharmaceutical compositions.

During the synthesis of the two peptides described in the Hungarian patent specification No. 185,263 the amino and carboxyl groups are protected by benzyl type protecting groups and the quanidino group of arginine is protected by a nitro group. In the last step all the protecting groups are removed by catalytic hydrogenation. The conditions under which this combination of the protecting groups works encumber the extension of the reaction and/or its realization on an obtained by hydrogenation is far below the present requirements. Accordingly, a new synthesis route was elaborated.

In the Hungarian patent application No. 3037/88 published under No. T/50195 only a tert-butyl-type protecting group is used during the synthesis of the structural and optical isomers of the peptides of the present invention and the guanidino group of arginine is protected by protonation. The protecting groups are removed in one step by using trifluoroacetic acid in a known manner. The synthesis route described in the patent application No. 3037/88 eliminates a large part of the side reactions of the synthesis described in the Hungarian patent specification No. 183,263 and the product obtained is more pure. However, the extension and the industrial scale realization of the process is expensive, involves several technical and environmental problems and spoils the quality.

In human therapy a peptide purity of more than 97% is generally acceptable and the quantity of a single contamination may surpass 0.5% only if its structure is known and its innocuity has been proved by toxicological tests.

According to the processes described in the Hungarian patent specification No. 185,263 and patent application No. 3037/88 the tripeptide Arg Lys Asp and the tetrapeptide Arg Lys Asp Val were separated and purified either after ion exchange by lyophilization or after evaporation by ethanolic treatment.

In both processes the tripeptide Arg Lys Asp and the tetrapeptide Arg Lys Asp Val were isolated in amorphous state. Both amorphous and air dried substances contain 70 to 85% of a peptide, the rest consists of water, acetic acid and ethanol. Lyophilized substances generally contain 15% of acetic acid. Both the water and the acetic acid content significantly depends on the technological circumstances (starting substance concentration, lyophilization program, drying time and temperature). The solvent content of the substance isolated by ethanol after the ion exchange reflects actively to the changes in the technological parameters and it did not succeed in removing the ethanol from some amorphous samples even by modifying the drying parameters within wide ranges. Their amorphous structure can also be proved by x-ray diffraction picture made with a powdery form. No sharp peaks showing crystalline structure can be observed. The thermogravimetric measurements and differential calorimetric test unambiguously prove that the peptides in question bind a part of the accompanying solvent by adsorption and thus their quantity and ratio varies in very wide ranges, presumably due to smaller undetermined changes of the technological parameters and e.g. by the changing moisture content of the surroundings. The last effect could have unambigously been proved by a thermogravimetric test. The slightly dissected wide stripe between 1700 and 1400 $cm^{-1}$ in the infrared spectrum shows the presence of water bound only by adsorption. Because of the amorphous state of the compounds even the quantity of the accompanying acetic acid is not stoichiometric and the quantity of the water and ethanol also fluctuates within wide ranges. In some countries the official stipulations for pharmaceutical starting substances allow neither a fluctuation of the quantity of the accompanying solvents within wide ranges nor the quantity of ethanol reaching 6 to 7%. The fluctuating peptide content of the products makes the adjustment of the desired dose uncertain during the preparation of the pharmaceutical compositions.

No crystalline substances of stoichiometric composition could be prepared by the known processes either through reprecipitation or treatment with a solvent of the oil obtained after ion exchange or of the solid, amorphous substance obtained from said oil.

SUMMARY OF THE INVENTION

In the knowledge cf the above it has surprisingly been found that the Arg Lys Asp and Arg Lys Asp Val obtained by the processes described in the Hungarian patent specification No. 185,263 and patent application No. 3037/88 can be made crystalline by a post-treatment with a water-ethanol mixture, containing also a small amount of acetic acid. According to the present invention, the crude, amorphous peptide Arg Lys Asp or Arg Lys Asp Val, respectively, is kept at room temperature in 5 to 20 unit volume of ethanol containing 0.5 to 4.0% by volume of acetic acid and 5 to 25% by volume of water, wherein the volume unit is calculated for the mass unit of the material and mass unit relates volume unit as g relates to ml, then the crystallized peptide is separated from the crystalline suspension, preferably after cooling.

One may preferably proceed by applying 10 units of volume of the above solvent mixture calculated for one mass unit of the crude peptide. The water content of the solvent mixture is adjusted in the case of peptide Arg Lys Asp preferably to 10% by volume and in the case of peptide Arg Lys Asp Val preferably to 19% by volume. This composition of the solvent system promotes the forming of crystals of a composition nearing "acetate-dihydrate" in the first case and "acetate-monohydrate" in the second case.

The process of the invention is preferably carried out by keeping the crude peptide in the beforehand prepared solvent mixture for several days until it becomes crystalline. The amorphous substance first slightly softens and becomes oily and then sets slowly crystalline. The crystallization may be completed by cooling. The crystalline peptide is separated preferably by filtration from the mother liquor. After filtration the crystalline substance is washed by aqueous ethanol and dried under air or in exsiccator.

When crystallizing the peptide Arg Lys Asp Val one may also proceed by dissolving the crude peptide in water containing an appropriate amount of acetic acid, then the calculated amount of ethanol is added to the solvent afterwards. The separation and processing of the precipitated crystalline Arg Lys Asp Val hydrate acetate product may be carried out as described above.

The process of the invention may successfully be applied in the case of both lyophilized crude peptides and crude peptides isolated by ethanol or by aqueous ethanol. The process is reproducible and may be enlarged to industrial scales.

The non-obviousness of the process of the invention is unambiguously proved by the fact that other, similar peptides, e.g. L-Arg L-Lys D-Asp acid, i.e. the diastereomer compound disclosed in the patent application No. 3037/88, cannot be made crystalline in this way.

The x-ray diffraction sprectrum of the crystalline peptides obtained is strongly dissected as related to the amorphous peptide used as starting substance. A great number of peaks relating to the crystalline structure appears therein. In the IR spectrum a sharp peak appears between wave numbers 3300 and 3400 cm$^{-1}$ indicating the presence of crystal water. The thermogravimetric curve taken with crystalline substances shows, in relation to amorphous substances, much stronger changes which take place in narrower temperature ranges.

The peptides prepared according to the process of the present invention possess very high purity. The purity of Arg Lys Asp dihydrate acetate surpasses 99%, the substance contains 0.7 to 0.8 mole/mole acetic acid, nearly 2 moles of water per mole of peptide water and less than 0.5% by weight of ethanol. The melting point of the different samples varies between 147° and 158° C. (during decomposition) in a wide range of maximum 4° C. The peptide Arg Lys Asp Val hydrate acetate contains about 0.8 mole/mole acetic acid, about 1 mole/mole water and less than 1% by weight of ethanol. The melting point of the different samples varies between 208° and 218 ° C. (during decomposition) in a wide range of maximum 4° C.

The crystalline state of the peptides prepared by the process of the invention is proved, in addition to their determined melting point, by their thermogravimetric and differential calorimetric examination and x-ray diffraction picture. These crystalline substances having a well definable composition are much more pure according to detailed quality control test than the amorphous products. Due to their crystalline state they are more stable, their storage is safer, they are not as sensitive to the environmental effects (temperature and humidity) as the amorphous peptides. The enteral administration of the known amorphous peptides require complicated and expensive encapsulating methods as the unsteady composition and the changeability caused by environmental effects excludes the preparation of tablets. On the contrary, the peptides prepared by the process of the invention are suitable for the preparation of solid forms of drugs, facilitating thereby their continuous oral administration.

The further details of the process according to the invention are illustrated by the following non-limiting examples. The abbreviations used in the specification correspond to the abbreviations generally used in the art [Biochem J., 219, 345 (1984)]. In the symbolic names of the compounds the amino acid groups are of L-configuration corresponding to the general labelling practice. The thin layer chromatography tests were carried out on prefabricated silica gel adsorbent (DC-Fertigplatten, Merck, FRG) with the following solvents (the ratios are always by volume; the stock solution is a 20:6:11 mixture of pyridine, acetic acid and water):

1. 3:7 mixture of n-butanol and stock solution
2. 2:8 mixture of n-butanol and stock solution
3. 1:1:1:1 mixture of n-butanol, acetic acid, ethyl acetate and water.

The chromatograms were developed by ninhydrine and after chlorination by a potassium iodide/tolydine reagent. The high pressure liquid chromatography measurements were performed on an equipment furnished with a Labor-MIM (a Hungarian company) type loop injector, a feeding pump and pressure indicator consisting of Gilson 802C and 302 units and an HP 3300A type integrator. For the separation a charge of the following parameters was used: grain size =6 μm, phase =C18, length =250 mm and internal diameter =4.6 mm (produced by Bioszeparációs Gmk, Hungary). As eluent a 10% aqueous phosphorous acid solution dihydrate acetate was used. The peptide Arg Lys Asp was tested with this solution while 3% by volume of acetonitrile was added to this eluent for the testing of the peptide Arg Lys Asp Val hydrate acetate. The measuring was carried out at a stream ratio of 1 ml/minute and the light absorption of the solution was detected at 212 nm.

The specific rotatory power was determined by a Perkin-Elmer 241 type polarimeter. All the evaporations were carried out on a Büchi type rotary vacuum evaporator on a water bath of 40° C. The melting points were determined by a Tottoli type (Büchi) measuring device.

The thermogravimetric and differential calorimetric measurements were carried out with a Mettler type TA 3000s DSC 20 T650 combined device. The x-ray diffraction pictures were taken by a Philips W 1840 type diffractometer.

The amino acid analysis of the end products was carried out in a Biotronic LC 5001 type device. The samples were hydrolyzed in a 6 moles/l hydrochloric acid solution at a temperature of 110 ° C. for 24 hours. The results were within the ±5% limit of error in all cases.

EXAMPLE 1

Crystallization of Arg Lys Asp hydrate acetate 31 g of an amorphous tripeptide containing 85% of peptide are sprinkled into 310 ml of a mixture containing 86 parts by volume of ethanol, 13 parts of water and 1 part of acetic acid and the adhered substance is broken up from time to time with a spatula until it fully transforms into granular crystals. The beginning of the crystal formation is visible to the naked eye after about 15 hours. After 3 days the mixture is put into a refrigerator for several hours and then the suspension is filtered, washed twice with 45 ml of the above described solvent mixture each and dried under air until its mass becomes steady. Thus 29.0 g of an end product is obtained which melts at 154° to 157° C. while decomposing. Its purity surpasses 99% as proved by both thin layer chromatography and high pressure liquid chromatography.

$R^1_f=0.08$; $R^2_f=0.15$; $R^3_f=0.20$.

Amino acid analysis:

Asp=1.00 (1), Lys=0.97 (1), Arg=1.01 (1).

$[\alpha]^{25}_D = +3.4°$ (c=1; 10% acetic acid);

$[\alpha]^{25}_D = 9.1°$ (c=1; acetic acid).

The peptide content of the different samples obtained by the repeated performance of the procedure described in the example amounted to 80 to 83%, their ethanol content was less than 0.5%, their water content varied between 6.5 and 8.0% and acetic acid content between 8 and 10%.

EXAMPLE 2

Crystallization of Arg Lys Asp Val hydrate acetate 13.8 g of an amorphous tetrapeptide containing 83% of peptide are treated with a mixture of 26 ml of water, 1.5 ml of acetic acid and 110 ml of ethanol as described in Example 1. The beginning of the crystal formation is visible to the naked eye after about 10 hours. After 2 days the mixture is put into a refrigerator for several hours, then the suspension is filtered, washed twice with 30 ml of 80% by volume of ethanol each and dried under air until the mass becomes steady. Thus 13.0 g of an end product is obtained which melts at 212° to 215° C. while decomposing. Its purity surpasses 99% as proved by both thin layer chromatography and high pressure liquid chromatography.

$R^1_f=0.15$; $R^3_F=0.30$.

Amino acid analysis:

Asp=1.00 (1), Lys=1.02 (1), Arg=1.01 (1), Val=0.97 (1).

$[\alpha]^{25}_D = -22.4°$ (c=1; 0.1 mol/1 acetic acid).

The peptide content of the different samples obtained by the repeated performance of the procedure described in the example amounted to 84 to 88%, their ethanol content was less than 1%, their water content varied between 3 and 5% and acetic acid content between 8 and 10%.

EXAMPLE 3

Crystallization of Arg Lys Asp Val hydrate acetate 13.8 g of an amorphous tetrapeptide containing 83% of peptide are dissolved in a mixture of 26 ml of water and 1.5 ml of acetic acid while shaking, then the solvent is diluted with 110 ml of ethanol. The crystalline title product slowly precipitates from the pure solution. The beginning of the nodule formation can be observed after 10 hours. After 2 days the mixture is kept in a refrigerator for several hours, then it is filtered and the precipitate is washed twice with 30 ml of 80% by volume of aqueous ethanol each and dried in air. Thus 12.8 g of a crystalline tetrapeptide is obtained which melts at 212° to 215° C. while decomposing. Its purity surpasses 99% as proved by both thin layer chromatography and high pressure liquid chromatography.

$R^1_f=0.15$; $R^3_f=0.30$.

Amino acid analysis:

Asp=1.01 (1), Val=0.98 (1), Lys=1.02 (1). Arg=1.01 (1).

$[\alpha]^{25}_D = -22.4°$ (c=1; 0.1 mole/1 acetic acid).

---

What is claimed is:

1. The crystalline peptide Arg Lys Asp dihydrate acetate having a purity of more than 99%, and having an IR absorption peak appearing between 3300 and 3400 cm$^{-1}$ indicating the presence of crystal water.

2. The crystalline peptide Arg Lys Asp Val hydrate acetate having a purity of more than 99%, having an IR absorption peak appearing between 3300 and 3400 cm$^{-1}$ indicating the presence of crystal water.

3. A pharmaceutical composition which regulates the immune system which comprises a therapeutically effective amount of the crystalline peptide Arg Lys Asp dihydrate acetate defined in claim 1 in combination with a pharmaceutically acceptable inert carrier.

4. A pharmaceutical composition which regulates the immune system which comprises a therapeutically effective amount of the crystalline peptide Arg Lys Asp Val hydrate acetate defined in claim 2 in combination with a pharmaceutically acceptable inert carrier.

5. A process for the preparation of a crystalline peptide Arg Lys Asp dihydrate acetate or a crystalline peptide Arg Lys Asp Val hydrate acetate, each having a purity of more than 99%, and having an IR absorption peak appearing between 3300 and 3400 cm$^{-1}$ indicating the presence of crystal water, which comprises the steps of:

(a) letting stand, at room temperature, a solvent mixture which is a 5 to 20 unit volume of ethanol containing 0.5 to 4.0% by volume of acetic acid, and 5 to 25% by volume of water, a starting peptide which is Arg Lys Asp or Arg Lys Asp Val, each containing 70 to 85% peptide, the balance consisting of water, acetic acid and ethanol, wherein the volume unit is calculated for the mass unit of the material, and mass unit relates to volume unit as g relates to ml, to form a crystalline suspension containing the crystalline peptide; and (b) separating the crystalline peptide from the crystalline suspension.

6. The process defined in claim 5 wherein following step (a), the crystalline suspension is cooled.

7. The process defined in claim 5 wherein according to step (a) 10 units by volume of solvent mixture are used per mass unit of the starting peptide.

8. The process defined in claim 5 wherein according to step (a) a solvent mixture containing 1% by volume of acetic acid is employed.

9. The process defined in claim 5 for the preparation of the crystalline peptide Arg Lys Asp dihydrate acetate wherein according to step (a), a solvent mixture containing 10% by volume of water is employed.

10. The process defined in claim 9 for the preparation of the crystalline peptide Arg Lys Asp dihydrate acetate wherein the starting peptide Arg Lys Asp is first dissolved in a water-acetic acid mixture and the calculated amount of the ethanol is added thereafter to form the solvent mixture.

11. The process defined in claim 5 for the preparation of the crystalline peptide Arg Lys Asp Val hydrate acetate wherein according to step (a), a solvent mixture containing 19% by volume of water is employed.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Peptide
        ( B ) LOCATION: 1..4
        ( D ) OTHER INFORMATION: /label=crystalline
        / note="Pure, crystalline product"

( x i ) SEQUENCE DESCRIPTION: SEQ ID NO:1:

Arg  Lys  Asp  Val
    1

( 2 ) INFORMATION FOR SEQ ID NO:2:

( i ) SEQUENCE CHARACTERISTICS:
        ( A ) LENGTH: 3 amino acids
        ( B ) TYPE: amino acid -continued

```
    ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Peptide
        ( B ) LOCATION: 1..3
        ( D ) OTHER INFORMATION: /label=crystalline
                / note="Pure, crystalline product"

( x i ) SEQUENCE DESCRIPTION: SEQ ID NO:2:

Arg  Lys  Asp
1
```